United States Patent [19]
Konishi et al.

[11] Patent Number: 4,877,263
[45] Date of Patent: Oct. 31, 1989

[54] HEIGHT CONTROL SYSTEM IN AUTOMOTIVE SUSPENSION SYSTEM WITH FEATURE OF CAPABILITY OF HEIGHT ADJUSTMENT IN LOCK CONDITION OF DRIVE WHEEL AND POWER TRAIN

[75] Inventors: Junkichi Konishi; Yasuhiro Shiraishi, both of Kanagawa, Japan

[73] Assignee: Nissan Motor Company, Limited, Yokohama, Japan

[21] Appl. No.: 186,223

[22] Filed: Apr. 26, 1988

[30] Foreign Application Priority Data

May 13, 1987 [JP] Japan .......................... 62-71144[U]

[51] Int. Cl.⁴ ............................................. B60G 11/26
[52] U.S. Cl. .................................. 280/707; 280/6.12; 280/DIG. 1; 180/41
[58] Field of Search ...................... 280/840, 6.1, 6.11, 280/6.12, 707, DIG. 1; 180/41

[56] References Cited

U.S. PATENT DOCUMENTS 4,519,169  5/1985  Smith ................................. 51/241 S
4,610,462  9/1986  Kumagai et al. .................... 280/707
4,659,104  4/1987  Tanaka et al. ....................... 280/707
4,718,695  1/1988  Kawagoe ............................ 280/707

FOREIGN PATENT DOCUMENTS

0114680  8/1984  European Pat. Off.
0114700  8/1984  European Pat. Off.

Primary Examiner—Kenneth R. Rice
Attorney, Agent, or Firm—Foley & Lardner, Schwartz, Jeffery, Schwaab, Mack, Blumenthal & Evans

[57] ABSTRACT

A vehicular height control system detects lock condition of a drive wheel and a power train. When the lock condition of the drive wheel and the power train is detected, magnitude of the height adjustment is limited within a predetermined magnitude which corresponds to magnitude of rotation of the drive wheel allowed by play in the power train. By adjusting the vehicular height within a limited range, height difference between the predetermined height range and the actual vehicular height can be reduced. On the other hand, by limiting magnitude of height adjustment in the drive wheel and the power train clocked condition, overshooting in the height adjustment can be successfully prevented.

31 Claims, 3 Drawing Sheets

HEIGHT CONTROL SYSTEM IN AUTOMOTIVE SUSPENSION SYSTEM WITH FEATURE OF CAPABILITY OF HEIGHT ADJUSTMENT IN LOCK CONDITION OF DRIVE WHEEL AND POWER TRAIN

BACKGROUND OF THE INVENTION

1. Field of the Invention

The present invention relates generally to a height control system in an automotive suspension system for adjusting or regulating the vehicular height to maintain within a predetermined height range. More specifically, the invention relates to a vehicular height control system which can perform height adjustment even when both of drive wheel and power train are locked.

2. Description of the Background Art

In the recent years, there have been developed various vehicular height control systems for regulating height of a vehicle body relative to road surface and whwreby for regulating vehicular attitude. In the typical construction of prior proposed vehicular height control system, vehicular height is monitored by a vehicle height sensor which monitors height of the vehicle body relative to the road surface or to a suspension member rotatably supporting a road wheel. Height adjustment is performed by adjusting suspension force to be exerted between the vehicle body and the suspension member to maintain the vehicular height within a predetermined height range. In practice, the suspension force is generated by means of a pressure chamber which is connected to a pressurized fluid source to introduce thereinto and discharge therefrom a pressurized working fluid, such as air, viscous oil and so forth.

In such vehicular height control system, suspension member is pivotally moved about its pivot during height adjustment for varying vehicle body height. This pivotal movement of the suspension member causes rotation of the road wheel. Therefore, in case of the road wheel is a drive wheel to be driven by an engine output through a power train, a drive shaft connecting a differential gear unit of the power train to the road wheel for distribution of the engine output torque, has to be rotated. In other words, unless causing rotation of the road wheel and drive shaft, height adjustment at the position of the drive wheel cannot be performed.

When height adjustment command is generated while the drive wheel is locked and power train is locked which tends to occur when an automatic power transmission operation mode is selected at parking position, suspension member is restricted pivotal movement so as not to cause height variation of the vehicle. However, due to presence of the height adjustment command, fluid pressure in the pressure chamber is continuously increased or decreased for adjusting suspension force. If lock on the drive wheel and the power train is released at this position, the drive wheel and the drive shaft becomes free from restriction and thus can rotate. This causes sudden change of vehicle height. This clearly degrades riding comfort of the vehicle.

Furthermore, when the drive wheel and power train is maintained for relatively long period of time, adjustment of the suspension force tends to overshoot to cause hunting in height adjustment. Namely, assuming the height adjustment command generated in the condition wherein the drive wheel and the power train are locked is DOWN command, the fluid pressure in the pressure chamber can be reduced excessively. Therefore, when lock of the drive wheel and the power train is released, the vehicle height drops across the lower limit of the predetermined height range to alternatively cause UP command. This subsequently cause height adjustment in UP direction. Such action tends to cause uncomfortable rid feeling for the vehicular occupants.

SUMMARY OF THE INVENTION

Therefore, it is an object of the present invention to provide a vehicular height control system which can solve the defect set forth above in the prior proposed systems.

Another and more specific object of the invention is to provide a vehicular height control system which is capable of height adjustment even when both of drive wheel and a power train is in locked condition appropriately for avoiding sudden change of the vehicular height when the lock is released.

In order to accomplish the aforementioned and other objects, a vehicular height control system, according to the present invention, detects lock condition of a drive wheel and a power train. When the lock condition of the drive wheel and the power train is detected, magnitude of the height adjustment is limited within a predetermined magnitude which corresponds to magnitude of rotation of the drive wheel allowed by play in the power train.

By adjusting the vehicular height within a limited range, height difference between the predetermined height range and the actual vehicular height can be reduced. On the other hand, by limiting magnitude of height adjustment in the drive wheel and the power tain clocked condition, overshooting in the height adjustment can be successfully prevented. According to one aspect of the invention, a height control system for an automotive suspension system, comprises a suspension system disposed between a vehicle body and a suspension member rotatably supporting a road wheel, the suspension system including means for varying suspension force to be exerted between the vehicle body and the suspension member, a sensor monitoring a relative distance between the vehicle body and the suspension member for producing a height indicative sensor signal;

a detector for detecting lock condition of the road wheel to produce a lock condition indicative signal, and a controlling means for receiving the sensor signal, and checking the value of the sensor signal with respect to a predereermined value for deriving a control signal to operate the varying means to adjust the suspension force for maintaining the relative distance between the vehicle body and the suspension member at a desired value, the controlling means being responsive to the lock condition indicative signal to limit magnitude of height adjustment with a predetermined range.

According to another aspect of the invention, a height control system for an automotive suspension system, comprises a suspension system disposed between a vehicle body and a suspension member rotatably supporting a drive wheel which is connected to a drive power source via a power train to be rotatingly driven by the output torque of the drive power source, the suspension system including means for varying suspension force to be exerted between the vehicle body and the suspension member, a sensor monitoring a relative distance between the vehicle body and the suspension member for producing a height indicative sensor signal, a detector for detecting lock condition of the drive wheel and the power train to produce a lock condition indicative signal, and a controlling means for receiving the sensor signal, and checking the value of the sensor signal with respect to a predetermined value for deriving a control signal to operate the varying means to adjust the suspension force for maintaining the reative distance between the vehicle body and the suspension member at a desired value, the controlling means being responsive to the lock condition indicative signal to limit magnitude of height adjustment with a predetermined range.

According to a further aspect of the invention, a height control system for an automotive suspension system, comprises a suspension system disposed between a vehicle body and a suspension member rotatably supporting a drive wheel which is connected to a drive power source via a power train to be rotatingly driven by the output torque of the drive power source, the suspension system including means for varying suspension force to be exerted between the vehicle body and the suspension member, the varying means comprises a hollow chamber communicated with a working fluid source to introduce and discharge working fluid in the hollow chamber for adjusting pressure of working fluid in the hollow chamber, which fluid pressure serves as the suspension force, and a pressure control valve disposed between the working fluid source and the hollow chamber for controlling introduction and discharging of working fluid into and from the hollow chamber for adjusting the suspension force and whereby adjusts the relative distance, a sensor monitoring a relative distance between the vehicle body and the suspension member for producing a height indicative sensor signal, a detector for detecting lock condition of the drive wheel and the power train to produce a lock condition indicative signal, and a controlling means for receiving the sensor signal, and checking the value of the sensor signal with respect to a predetermined value for deriving a control signal to operate the varying means to adjust the suspension force for maintaining the relative distance between the vehicle body and the suspension member at a desired value, the controlling means being responsive to the lock condition indicative signal to limit magnitude of height adjustment with a predetermined range.

According to a still further aspect of the invention, a height control system for an automotive suspension system, comprises a suspension system disposed between a vehicle body and a suspension member rotatably supporting a drive wheel which is connected to a drive power source via a power train to be rotatingly driven by the output torque of the drive power source, the suspension system including means for varying suspension force to be exerted between the vehicle body and the suspension member, a sensor monitoring a relative distance between the vehicle body and the suspension member for producing a height indicative sensor signal, a first detector for detecting lock condition of the drive wheel to produce a first lock condition indicative signal, a second detector for detecting lock condition of the power train to produce a second lock condition indicative signal, and a controlling means for receiving the sensor signal, and checking the value of the sensor signal with respect to a predetermined value for deriving a control signal to operate the varying means to adjust the suspension force for maintaining the relative distance between the vehicle body and the suspension member at a desired value, the controlling means limiting magnitude of height adjustment with a predetermined range when both of the first and second lock condition indicative signals are detected.

In the practical construction, the first detector monitors brake condition on the road wheel. Therefore, the first detector comprises a parking brake switch detective of application of a parking brake to produce the lock condition indicative signal and/or a foot brake switch detective of application of a foot brake to produce the lock condition indicative signal.

On the other hand, the second detector may comprise an automatic transmission operational range selected at park position to produce the lock condition indicative signal.

In practice, the controlling means is responsive to the lock condition indicative signal to set a given period of time during which height adjustment is enabled and to disable height adjustment after expiration of the given period of time for limiting magnitude of height control. In this case, the magnitude to permit height adjustment may correspond to the possible pivotal motion magnitude of the suspension member allowed by play and possible or acceptable torsion in the power train.

DESCRIPTION OF THE PREFERRED EMBODIMENT

Figure 1:
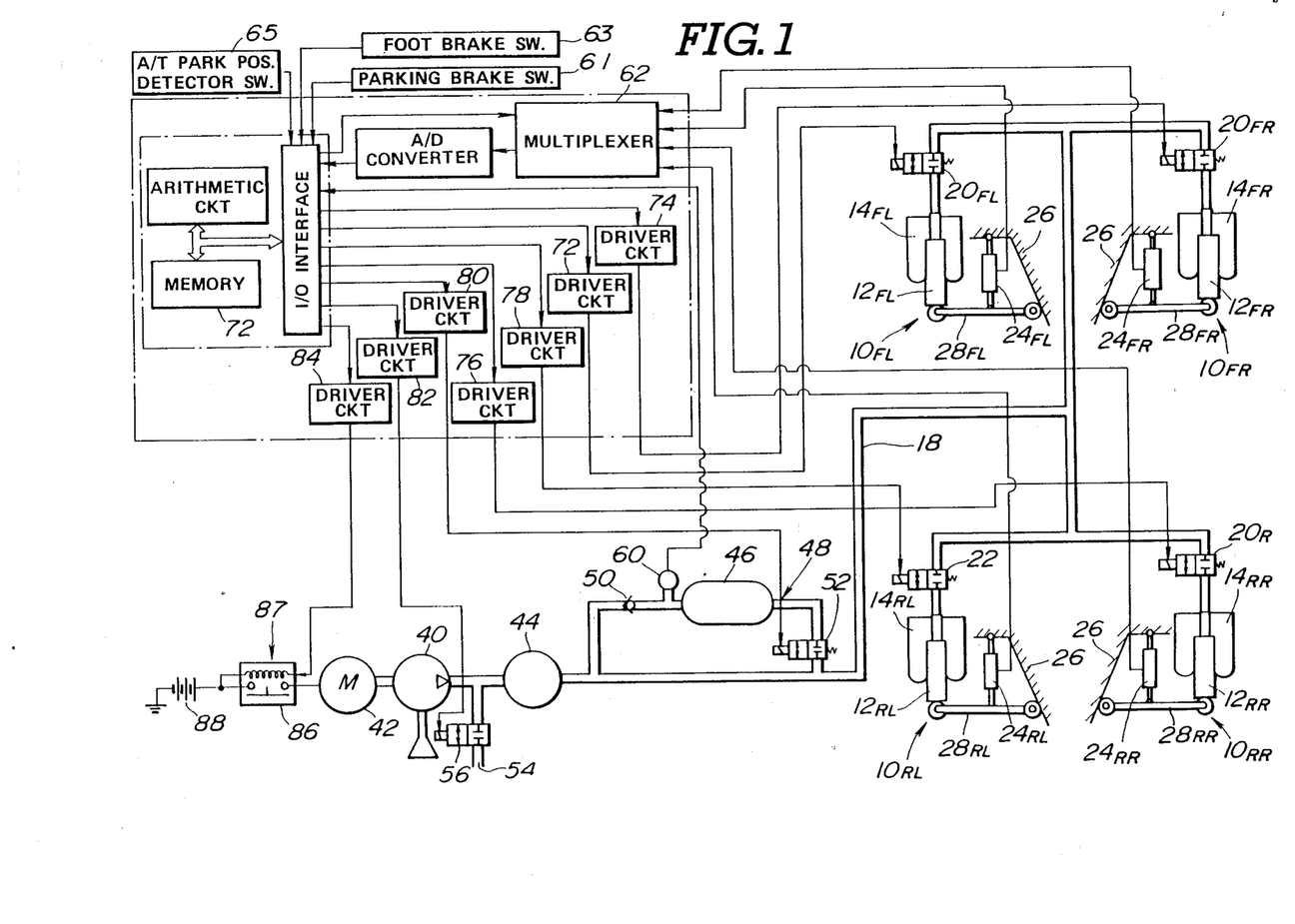
FIG. 1 is a block diagram of the preferred embodiment of a height control system in an automotive suspension system, according to the present invention.

Referring now to the drawings, particularly to FIG. 1, the preferred embodiment of a height control system in an automotive suspension system, according to the present invention, employs suspension system $10_{FL}$, $10_{FR}$, $10_{RL}$ and $10_{RR}$ for rotatably supporting front-left, front-right, rear-left and rear-right vehicular wheels. The suspension systems $10_{FL}$, $10_{FR}$, $10_{RL}$ and $10_{RR}$ include suspension struts $12_{FL}$, $12_{FR}$, $12_{RL}$ and $12_{RR}$ which include shock absorbers and height control actuator means $14_{FL}$, $14_{FR}$, $14_{RL}$ and $14_{RR}$.

In the shown embodiment, the vehicle to which the preferred embodiment of the height control system is applied, has a rear wheel drive layout. Therefore, rear wheels (not shown) are drive wheel to be driven by an engine output. Therefore, when height adjustment is taken place for the rear suspension systems $10_{RL}$ and $10_{RR}$, it causes corresponding magnitude of rotation of drive shafts in a power train.

The actuator means $14_{FL}$, $14_{FR}$, $14_{RL}$ and $14_{RR}$ generally comprise pressure chambers filled with a working fluid. In the preferred embodiment, the pressure chambers $14_{FL}$, $14_{FR}$, $14_{RL}$ and $14_{RR}$ are filled with gas, such as an air. Each of the pressure chambers $14_{FL}$, $14_{FR}$, $14_{RL}$ and $14_{RR}$ is connected to a pressurized air source 16 via pressure supply system 18. Height control valve means $20_{FL}$, $20_{FR}$, $20_{RL}$ and $20_{RR}$ are disposed within the pressure supply system 18 for controlling air pressure to be supplied for respectively corresponding pressure chambers $14_{FL}$, $14_{FR}$, $14_{RL}$ and $14_{RR}$. As seen from FIG. 1, the height control valve means $20_R$ is designed for commonly adjusting the air pressure in the pressure chambers $14_{RL}$, $14_{RR}$ of the rear suspension systems $10_{RL}$ and $10_{RR}$.

Height sensors $24_{FL}$, $24_{FR}$, $24_{RL}$ and $24_{RR}$ are provided at positions where the respective front-left, front-right, rear-left and rear-right suspension systems $10_{FL}$, $10_{FR}$, $10_{RL}$ and $10_{RR}$ are provided for monitoring relative height between vehicle body 26 and suspension members $28_{FL}$, $28_{FR}$, $28_{RL}$ and $28_{RR}$ which are connected to the vehicular wheels. Respective height sensors $24_{FL}$, $24_{FR}$, $24_{RL}$ and $24_{RR}$ produces vehicle height indicative signals $S_{FL}$, $S_{FR}$, $S_{RL}$ and $S_{RR}$. The vehicle height indicative signals $S_{FL}$, $S_{FR}$, $S_{RL}$ and $S_{RR}$ of the height sensors $24_{FL}$, $24_{FR}$, $24_{RL}$ and $24_{RR}$ are fed to a controller 30.

The controller 30 includes a discriminator stage and a control signal generator stage. The vehicle height indicative signals $S_{FL}$, $S_{FR}$, $S_{RL}$ and $S_{RR}$ are input to the discriminator stage of the controller. In the discriminator stage, each of the vehicle height indicative signals $S_{FL}$, $S_{FR}$, $S_{RL}$ and $S_{RR}$ is compared with a maximum height indicative upper criterion $H_U$ and a minimum height indicative lower criterion $H_L$ to discriminate whether the vehicle height as represented by the corresponding vehicle height indicative signal is within a target height range defined by the upper and lower criteria $H_U$ and $H_L$.

When the vehicle height level is out of the target height range, the control signal generator stage is triggered for operation. In response to initiation of the operation of the control signal generator stage, a communication valve control signal is, at first, output to the communication valve 22 to open the latter. In response to the height control signal of the control signal generator stage, respective height control valve means $20_{FL}$, $20_{FR}$, $20_{RL}$ and $20_{RR}$ are operated to adjust the vehicle height level at respectively corresponding wheel positions to be within the target height range.

As shown in FIG. 1, the air source 16 comprises a compressed air supply network including a motor driven compressor 40 which is associated with an electric motor 42 to be driven by the driving force transmitted therefrom. The compressor 40 is connected to the pressure supply passage system 18. An air dryer 44 is disposed in the pressure supply passage system 18 and downstream of the compressor for drying the air fed from the compressor. In addition, a pressure accumulator 46 is provided in a pressure accumulation system 48 which is in communication with the pressure supply passage system 18 at both ends. An one-way check valve 50 is provided in the pressure accumulation system 48 and upstream of the pressure accumulator 46. An electromagnetically actuated pressure accumulation control valve 52 is provided downstream of the pressure accumulator 46.

The pressure supply passage system 18 includes a ventilation port 54, at which a ventilation control valve 56 is provided for opening and closing the port.

As seen from FIG. 1, the height control valves means $20_{FL}$, $20_{FR}$, $20_{RL}$ and $20_{RR}$ comprise electromagnetically actuated valves. The height control valves $20_{FL}$, $20_{FR}$, $20_{RL}$ and $20_{RR}$, the pressure accumulation control valve 52 and the ventilation control valve 56 are respectively connected to the controller 30 to be controlled respective valve positions. The height control valves $20_{FL}$, $20_{FR}$, $20_{RL}$ and $20_{RR}$, employed in the shown embodiment, are so designed as to open while they are activated, to establish communication between the pressure chambers $14_{FL}$, $14_{FR}$, $14_{RL}$ and $14_{RR}$ and the pressure supply passage system 16 and to close while they are deactivated, to block the communication. The accumulation control valve 52 is so designed as to be activated to open for establishing communication between the pressure accumulator 46 and the pressure supply passage means 16 and to be deactivated to close for blocking the communication. The ventilation control valve 56 is designed to be activated to open the valve for exposing the pressure supply passage means 16 to the atmosphere for ventilation of the pressurized air through the ventilation port 54 and to be deactivated to shut the valve.

In order to monitor the pressure accumulated on the pressure accumulator 46, a pressure sensor 60 is provided. The pressure sensor 60 is designed for generating an accumulated pressure indicative signal to be input to the controller 30 as a compressor control parameter.

The height sensors $24_{FL}$, $24_{FR}$, $24_{RL}$ and $24_{RR}$, employed in the shown embodiment, comprise stroke sensors disposed between the vehicle body 26 and the suspension members $28_{FL}$, $28_{FR}$, $28_{RL}$ and $28_{RR}$. Each of the stroke sensors $24_{FL}$, $24_{FR}$, $24_{RL}$ and $24_{RR}$ may comprise an electrostatic capacity-type stroke sensor as shown in FIGS. 2 and 3, for example.

Figure 2:
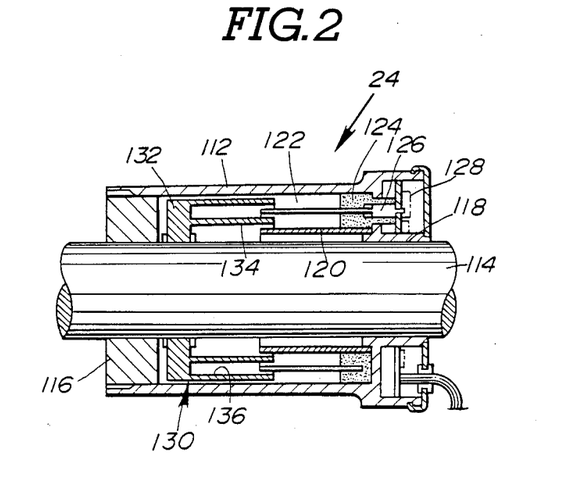
FIG. 2 is a partial and longitudinal section of one example of a vehicle height sensor to be employed in the preferred embodiment of the vehicle height control system according to the invention.
Figure 3:
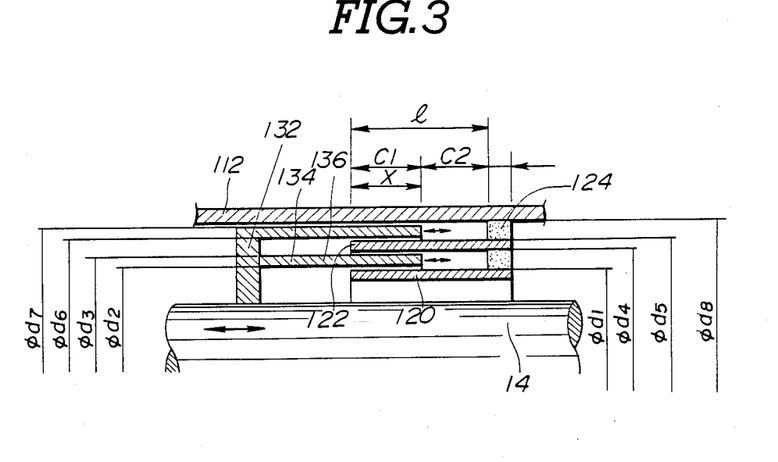
FIG. 3 is an enlarged section of the major part of the vehicle height sensor of FIG. 2.

As shown in FIGS. 2 and 3, the preferred example of the electrostatic capacity-type stroke sensor is generally represented by the reference numeral '110'. The electrostatic capacity-type stroke sensor 110 is designed for measuring relative stroke between a cylindrical member 112 and a rod member 114. In the shown construction, the rod member 114 is coaxially arranged through the cylindrical member 112 and thrustingly supported by means of supporting plug 116 and a cylindrical support section 118 integrally formed with the cylindrical member.

Both of the cylindrical member 112 and the rod member 114 are made of electrically conductive material and, in turn, electrically isolated to each other.

Inner and outer cylinders 120 and 122 are coaxially disposed between the cylindrical member 112 and the rod member 114. The cylindrical member 112, the outer cylinder 122, the inner cylinder 120 and the rod member 114 are coaxially arranged in spaced apart relationship and held in place by means of an annular support 124 which is made of an electrically insulative material.

The inner cylinder 120 is electrically connected to the cylindrical member 112 to constitute therewith a grounding electrode. On the other hand, the outer cylinder 122 is connected to a terminal 126 which is, in turn, connected to a sensor circuit 128. In the shown embodiment, the sensor circuit 128 comprises a RC oscillator. The outer cylinder 122 is designed to function as positive electrode. The sensor circuit 128 is also connected to the grounding electrode formed by the inner cylinder 120 and the cylindrical member 112 to be grounded therethrough.

With the plug 116, the cylindrical supporting section and the insulative support 124 establishes gas tight seal. A gaseous state dielectric material which has stable dielectric constant is filled in the enclosed space.

On the other hand, a dielectric member 130 is provided for movement with the rod member 114. The dielectric member comprises a radially extending disk-shaped section 132 and coaxially arranged inner and outer cylindrical sections 134 and 136. The inner diameter $\phi d_2$ of the inner cylindrical section 134 of the dielectric member 130 is greater than the outer diameter $\phi d_1$ of the inner cylinder 120 and the outer diameter $\phi d_3$ is smaller than the inner diameter $\phi d_4$ of the outer cylinder 122 so that the inner cylindrical section 134 may enter into the annular space defined between the inner and outer cylinders 120 and 122, as shown in FIG. 2. On the other hand, the inner diameter $\phi d_6$ of the outer cylindrical section 136 is greater than the outer diameter $\phi d_5$ of the outer cylinder 122 and the outer diameter $\phi d_7$ is smaller than the inner diameter $\phi d_8$ of the cylindrical member 112 so that the outer cylindrical section may enter into the annular space defined between the outer cylinder 122 and the cylindrical member. On the other hand, the disk-shaped section 132 is rigidly fixed to the outer periphery of the rod member 114 so that the dielectric member 130 may be moved according to movement of the rod member 114.

With the construction set forth above, the electrostatic capacity Ct is created between the inner and outer cylinders 120 and 122 and the inner and outer cylindrical sections 134 and 136 of the dielectric member 130 while relative displacement between the cylindrical member 112 and the rod member 114 occurs.

Here, assuming the possible maximum relative stroke between the cylindrical member 112 and the rod member 114 is l, as shown in FIG. 2, the relative dielectric constant of the dielectric member is $e_2$; and the relative dielectric constant of the gaseous dielectric material is $e_1$. It is further assumed that the electrostatic capacity of overlapping portion between the inner and outer cylindrical sections 134 and 136 and the inner and outer cylinders 120 and 122 is $C_1$; the electrostatic capacity of the portions of the inner and outer cylinders 120 and 122 outside of the inner and outer cylindrical sections 134 and 136 is $C_2$; and the electrostatic capacity of the portion where the inner and outer cylinders 120 and 122 are supported is $C_3$. In this case, the electrostatic capacities $C_t$, $C_1$ and $C_2$ can be respectively illustrated by the following equations:

$$C_t = C_1 + C_2 + C_3 \tag{1}$$

$$C_1 = 2\pi e_0 \times [1/\{(e_2 - 1/e_1)\ln.d_3/d_2 + 1/e_1.\ln d_4/d_1\} + \{1/(1/e_2 - 1/e_1)\ln.d_7/d_6 + 1/e_1.\ln d_8/d_5\}] \tag{2}$$

$$C_2 = 2\pi e_0 (1-x).$$
$$[1/\{(1-e_1)\ln(d_4/d_1)\} + 1/\{(1-e_1)\ln(d_8/d_5)\}] \tag{3}$$

where $e_0$ is dielectric constant in vacuum
Here, it is assumed:

$$[1/\{(1/e_2 - 1/e_1)\ln.d_3/d_2 /d_2 + 1/e_1.\ln d_4/d_1\} + \{1/(1/e_2 - 1/e_1)\ln.d_7/d_6 e_1.\ln d_8/d_5\}] = A; \text{ and}$$

$$[1/\{(1-e_1)\ln(d_4/d_1)\} + 1/\{(1-e_1)\ln(d_8/d_5)\}] = B$$

A and B are both constant. The equations (2) and (3) can be modified utilizing A and B, the electrostatic constant Ct can be illustrated by:

$$Ct = 2\pi e_0 x(A-B) + 2\pi e_0 lB + C_3 \tag{4}$$

As will be appreciated herefrom, the electrostatic constant Ct is variable in proportion to the stroke x.

As set forth, the detector circuit comprises the RC oscillator whose oscillation cycle period can be described by:

$$T = (1/K)RC \tag{5}$$

where K is constant.
From this the frequency output characteristics of the RC oscillator can be described by:

$$T = (R/K)2\pi e_0 x(A-B) + C_0 \tag{6}$$

where $C_0 = 2\pi e_0 lB + C_3$

As will be appreciated from the foregoing equations, the frequency oscillation cycle period T is proportional to the relative displacement stroke x. Therefore, by monitoring the frequency oscillation cycle period T, the stroke x can be detected.

Here, the diameters $\phi d_1$ through $\phi d_8$ can be varied depending upon the temperature of atmosphere due to thermal expansion. Among those variable dimensions, the radios $\phi d_3/\phi d_2$ and $\phi d_7/\phi d_6$ are regarded constant despite of various rate of thermal expansions.

Similarly, the radios $\phi d_4/\phi d_1$ and $\phi d_8/\phi d_5$ are regarded constant.

On the other hand, the dielectric constants $e_1$ and $e_2$ of the gaseous dielectric material filled in the space defined in the cylindrical member and the dielectric member 130 can be made substantially in constant at any temperature range by appropriately selecting the materials. For example, the dielectric material which exhibits stable dielectric constant in relation to temperature variation may be selected among air or resin, such as polyacetal resin, polypropylene resin. Therefore, as the gaseous dielectric material, the air may be used in the preferred embodiment so as to avoid influence of the temperature variation and to obtain stable dielectric constant thereof.

However, as the dielectric material for forming the dielectric member 130, a material which can provide higher resolution in measurement of the relative stroke between the rod member and the cylindrical member, is preferred. In order to obtain higher resolution, greater electrostatic capacity to be established becomes necessary. This, in turn, requires higher dielectric constant of the dielectric material forming the dielectric member 130. Satisfactorily high dielectric constant is obtainable by utilizing inorganic material, such as mica. Such inorganic material is known to have substantially high dielectric constant but is know as expensive material and as difficult material for machining and/or mass-production. On the other hand, synthetic resins are less expensive and easy for forming a desired shape. However, the synthetic resin generally have low or insufficient dielectric constant as required for the stroke sensor of the type disclosed hereabove.

In this view, the preferred embodiment of the stroke sensor, according to the present invention, employs a composite dielectric material which is a composition of the synthetic resin material and inorganic material. As a resin material to form the composition, thermoplastic resin, such as polypropylene, polyacetal, polybuthylene terephtalate, polyphenylene sulfide and so forth are preferred in view of solubility with the inorganic material. As inorganic material, ceramics are used.

Each of the stroke sensors $24_{FL}$, $24_{FR}$, $24_{RL}$ and $24_{RR}$ are connected to the controller 30 via a multiplexer 62 and an analog-to-digital (A/D) converter 64. On the other hand, the controller 30 comprises a microprocessor 66 having an input/output interface 68, an arithmetic circuit 70, such as CPU, and a memory 72, such as ROM, RAM, register and so forth. The input/output interface 68 is connected to the A/D converter to receive one of the height indicative signal from the corresponding one of the stroke sensors $24_{FL}$, $24_{FR}$, $24_{RL}$ and $24_{RR}$ as selected by the multiplexer 62. The multiplexer 62, is designed to receive a clock signal output from the microprocessor to select one of the height indicative signals in a given order and at a given timing.

In addition, the controller 30 employed in the shown embodiment of the height control system, is connected to a parking brake switch 61, a foot brake switch 63 and an automatic power transmission park position detector switch 65. The parking brake switch 61 is designed to output a parking brake position indivative signal while is held LOW level while the parking brake is in released condition and is switched into HIGH level when the parking brake is applied. The foot brake switch 63 is designed to detect a foot brake position to produce a LOW level foot brake position indicative signal while the a brake is not applied and to produce a HIGH level foot brake position indicative signal when the foot brake is applied. On the other hand, the automatic transmission park position detector switch 65 is designed to produce a LOW level park position indicative signal when a automatic transmission operational mode is other than park position, e.g. neutral position, reverse gear range position, first gear range position, second gear range position, top gear range position or overdrive gear range position, and to produce a HIGH level park position indicative signal when the park position of the automotic power transmission is selected.

As will be appreciated that the parking brake switch 61 and the foot brake switch 63 serve as detectors for detecting locked condition of the road wheels. It should be noted that, since the shown embodiment specifically concerns height adjustment at drive wheel, the parking brake switch 61 may be employed as a lock condition detector for detecting lock condition of the drive wheel.

The input/output interface 68 is also connected to driver circuits 72, 74, 76, 78, 80, 82. to feed thereto control signals. The driver circuits, 72, 74, 76 and 78 are respectively connected to the height control valves $20_{FL}$, $20_{FR}$, $20_{RL}$ and $20_{RR}$ to feed thereto height control driver signals. The driver circuits 72, 74, 76 and 78 output HIGH level height control driver signals when the height level of respectively corresponding vehicle body portions is out of the target height range and, otherwise, output LOW level height control driver signals. Therefore, the height control valves $20_{FL}$, $20_{FR}$, $20_{RL}$ and $20_{RR}$ are responsive to the HIGH level height control signal to be activated and to the LOW level height control signal to be deactivated. Furthermore, the driver circuit 80 is connected to the pressure accumulation control valve 52 to feed a HIGH level accumulator control signal to open the latter for establishing communication between the pressure accumulator 46 and the pressure supply system 18 and to feed a LOW level accumulator control signal to close the latter for blocking the communication.

The driver circuit 82 is connected to the ventilation control valve 56 to open in order to expose the pressure supply system 18 to the atmosphere by HIGH level ventilation control signal and to shut for closing the pressure supply system.

In addition, the microprocessor 66 detects the pressure in the pressure accumulator 46 dropping lower than a predetermined pressure to generate a compressor control signal. The compressor control signal is fed to a driver circuit 84 via the input/output interface 68. The driver circuit 84 is connected to a power supply control relay 86 which establishes and blocks electric connection between the electric motor 42 and a vehicular battery 88. In response to the compressor control signal, the driver circuit 84 produces a compressor drive signal for energizing the power supply control relay 86 for establishing electric connection between the battery 88 and the motor 42 to drive the motor. As a result, the compressor 40 is driven by the driving force of the motor 42 to supply the pressure to the pressure accumulator 46.

Figure 4:
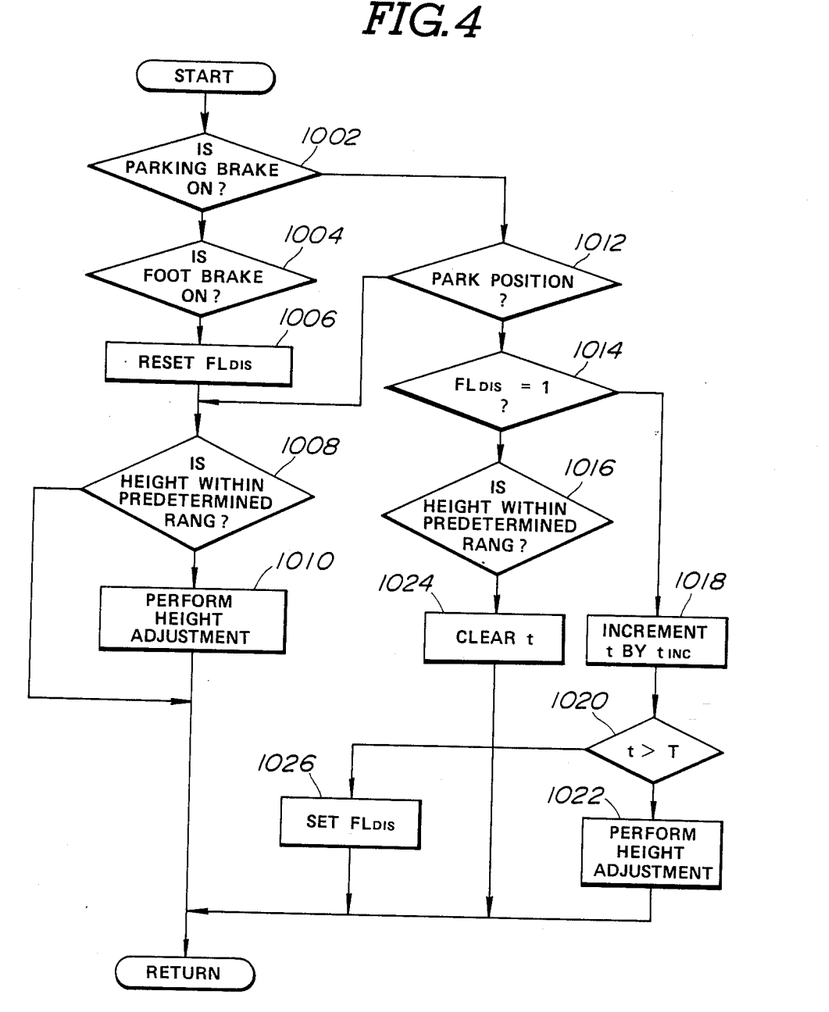
FIG. 4 is flowchart showing a sequence of a vehicle height control program for controlling height position of a vehicle body relative to a suspension member.

Practical height control operation to be performed by the controller 30 will be discussed herebelow with reference to FIG. 5 which shows a height control program to be cyclically and intermittently executed by the microprocessor 66 in the control system. The shown program is designed to be executed every given timing, e.g. every 20 ms. In the practical height control operation, height of the vehicle at one of the suspension systems $10_{FL}$, $10_{FR}$, $10_{RL}$ and $10_{RR}$ corresponding to one of the height indicative signal $S_{FL}$, $S_{FR}$, $S_{RL}$ and $S_{RR}$ selected by the multiplexer 62.

Immediately after starting execution of the height control program, parking brake position indicative signal level is checed at a step 1002. If the parking brake position indicative signal level is LOW which represents the release position of the parking brake, the foot brake position indicative signal level is checked at a step 1004. When the foot brake position indicative signal level is also LOW level, process goes to a step 1006 to reset a height adjustment disabling flag $FL_{DIS}$. After resetting the height adjustment disabling flag $FL_{DIS}$ at the step 1006, process goes to a step 1008 to compare the height indicative signal with the upper and lower height criteria $H_U$ and $H_L$ to judge whether the vehicular height is within a predetermined height range or not.

Here, it should be noted that the predetermined height range is determined with respect to a preset target height which may serve as a center height in the predetermined height range. Therefore, the precision of vehicular attitude control can be determined by selecting the width of the acceptable height range relative to the target height. When substantially precise height control and consequently the attitude control is desired, it may be possible to adjust the vehicle height at the target height instead of utilizing the acceptable height range. Based on the result of comparison of the actually monitored vehicle height as represented by the height indicative signal value, and the upper and lower height criteria $H_U$ and $H_L$, UP and DOWN command is generated to perform height adjustment at a step 1010, in case the vehicle height out of the predetermined height range is detected as checke at the step 1008.

Namely, when the vehicular height indicative signal is smaller than the lower height criterion $H_L$, UP command is issued. The microprocessor 66 is then responsive to the UP command to check the pressure in the pressure accumulator 46. When the pressure in the pressure accumulator 46 is sufficiently high to increase the pressure in the corresponding one of pressure chambers $14_{FL}$, $14_{FR}$, $14_{RL}$ and $14_{RR}$, the control signal is fed to the accumulation control valve 52 to open. On the other hand, when the fluid pressure in the pressure accumulator 46 is not sufficient, the microprocessor 66 outputs HIGH level control signal to the relay 86 to drive the pump motor 42 to drive compressor 40. Simultaneously, HIGH level control signals are fed to corresponding one of the height control valves $20_{FL}$, $20_{FR}$, $20_{RL}$ and $20_{RR}$. On the other hand, when the height indicative signal value is greater than the upper height criterion $H_U$, DOWN command is produced. The microprocessor 66 is responsive to this DOWN command to output control signal to the ventilation control signal to open the ventilation control valve 56. Also, control signal is fed to one of the height control valves $20_{FL}$, $20_{FR}$, $20_{RL}$ and $20_{RR}$ to open to reduce the fluid pressure in corresponding one of the pressure chambers $14_{FL}$, $14_{FR}$, $14_{RL}$ and $14_{RR}$.

On the other hand, when the vehicle height as represented by the height indicative signal held in the predetermined height range is detected as checked at the step 1008, process goes END.

When the parking brake position indicative signal as checked at the step 1002 is HIGH level or the foot brake position indicative signal as checked at the step 1004 is HIGH level, which represents locked condition of the road wheel (drive wheel), process goes to a step 1012. At the step 1012, the automatic power transmission park position indicative signal level is checked. If the automatic power transmission park position indicative signal level, as checked at the step 1012 is LOW level, which represents that the power train is not locked, process goes to the step 1006 to perform normal state height adjustment operation.

On the other hand, when the automatic transmission park position indicative signal level is HIGH as checked at the step 1012, the height adjustment disabling flag $FL_{DIS}$ is checked at a step 1014. When set condition of the height adjustment disabling flag $FL_{DIS}$ is set as checke at the step 1014, process goes END. On the other hand, the reset condition of the height adjustment disabling flag $FL_{DIS}$ is detected at the step 1014, the height indicative signal value is compared with the upper and lower height criteria $H_U$ and $H_L$ at a step 1016.

When the height indicative signal value is out of the predetermined range as defined by the upper and lower height criteria $H_U$ and $H_L$, a value t of a cycle counter 71 in the controller 30 is incremented by a given value $t_{inc}$ at a step 1018. Then, the cycle counter value t is compared with a timer-up reference value T which is set to define a period in which height adjustment in lock condition of the drive wheel and the power train is permitted, at a step 1020. In practice, the height adjustment permitting period as represented by the time-up reference T is set in view of the possible magnitude of pivotal movement of the suspension member allowed by play or possible torsion in power train.

When the cycle counter value t is smaller than or equal to the time-up reference value T, UP or DOWN command is output to perform height adjustment in substantially the same manner as thaty performed in the step 1010, at a step 1022.

When the height indicative signal value as checked at the step 1016 is within the range defined by the upper and lower height criteria $H_U$ and $H_L$, the cycle counter value is cleared at a step 1024. Thereafter, process goes END. On the other hand, when the cycle counter value t is greater than the time-up reference value T, as checked at the step 1020, the height adjustment disabling flag $FL_{DIS}$ is set at a step 1026 and then process goes to the step 1024 to clear the cycle counter value t.

It should be appreciated that the height control to be performed by the microprocessor at the steps 1010 and 1022 will incorporate various control parameters in addition to the vehicular height. Practical height control processes employing various height control parameters have been disclosed in the patents and co-pending applications, listed herebelow. The disclosure of the below-listed references are herein incorporated by reference.

U.S. Pat. No. 4,519,169
European Patent First Publication No. 01 14 680
European Patent First Publication No. 01 14 700
U.S. Pat. No. 4,659,104
U.S. Pat. No. 4,718,695
U.S. Ser. No. 906,239, filed on Sept. 12, 1986
U.S. Ser. No. 056,761, filed on June 2, 1987
German Patent First Publication No. 37 15 441
U.S. Ser. No. 120,964, filed on Nov. 16, 1987.

As will be appreciated, according to the present invention, vehicular height can be adjusted within a range permitted by play and/or possible or acceptable torsion in the power train to reduce the difference between the actual vehicle height and the associated upper or lower criterion defining the predetermined height range. This reduces necessary magnitude of height adjustment to be performed after lock release of the drive wheel and the power train. Further, ore, limiting of the height adjustment magnitude during the period while the drive wheel and the power train are locked, overshooting in height adjustment can be successfully prevented.

Therefore, the invention fulfills all of the objects and advantages sought therefor.

While the present invention has been disclosed in terms of the preferred embodiment in order to facilitate better understanding of the invention, it should be appreciated that the invention can be embodied in various ways without departing from the principle of the invention. Therefore, the invention should be understood to include all possible embodiments and modifications to the shown embodiments which can be embodied without departing from the principle of the invention set out in the appended claims.

For example, though the show embodiment limits the magnitude of height adjustment during lock condition of the drive wheel and the power train by limiting the time to perform height control, it may be possible to limit the magnitude of height control per se. This can be done by modifying the target height toward which the height control is to be performed based on the instantaneous actual vehicle height at the occurence of the UP or DOWN command under lock condition of the drive wheel and the power train.

What is claimed is:

1. A height control system for an automotive suspension system, comprising:
a suspension system disposed between a vehicle body and a suspension member rotatably supporting a road wheel, said suspension system including means for varying suspension force to be exerted between said vehicle body and said suspension member;

a sensor monitoring a relative distance between said vehicle body and said suspension member for producing a height indicative sensor signal;

a detector for detecting lock condition of said road wheel to produce a lock condition indicative signal; and a controlling means for receiving said sensor signal, and checking the value of said sensor signal with respect to a predetermined value for deriving a control signal to operate said varying means to adjust said suspension force for maintaining said relative distance between said vehicle body and said suspension member at a desired value, said controlling means being responsive to said lock condition indicative signal to limit magnitude of height adjustment with a predetermined range.

2. A height control system as set forth in claim 1, wherein said detector monitors brake condition on said road wheel.

3. A height control system as set forth in claim 2, wherein said detector comprises a parking brake switch detective of application of a parking brake to produce said lock condition indicative signal.

4. A height control system as set forth in claim 2, wherein said detector comprises a manually operable brake switch detective of application of a manually operable brake to produce said lock condition indicative signal.

5. A height control system as set forth in claim 4, wherein said detector comprises a foot brake switch detective of application of a foot brake to produce said lock condition indicative signal.

6. A height control system as set forth in claim 1, wherein said controlling means is responsive to said lock condition indicative signal to set a given period of time during which height adjustment is enabled and to disable height adjustment after expiration of said given period of time.

7. A height control system for an automotive suspension system, comprising:

a suspension system disposed between a vehicle body and a suspension member rotatably supporting a drive wheel which is connected to a drive power source via a power train to be rotatingly driven by the output torque of said drive power source, said suspension system including means for varying suspension force to be exerted between said vehicle body and said suspension member;

a sensor monitoring a relative distance between said vehicle body and said suspension member for producing a height indicative sensor signal;

a detector for detecting lock condition of said drive wheel and said power train to produce a lock condition indicative signal; and a controlling means for receiving said sensor signal, and checking the value of said sensor signal with respect to a prederermined value for deriving a control signal to operate said varying means to adjust said suspension force for maintaining said relative distance between said vehicle body and said suspension member at a desired value, said controlling means being responsive to said lock condition indicative signal to limit magnitude of height adjustment with a predetermined range.

8. A height control system as set forth in claim 7, wherein said detector monitors brake condition on said road wheel.

9. A height control system as set forth in claim 8, wherein said detector comprises a parking brake switch detective of application of a parking brake to produce said lock condition indicative signal.

10. A height control system as set forth in claim 8, wherein said detector comprises a foot brake switch detective of application of a foot brake to produce said lock condition indicative signal.

11. A height control system as set forth in claim 7, wherein said detector comprises an automatic transmission operational range selected at park position to produce said lock condition indicative signal.

12. A height control system as set forth in claim 8, wherein said detector also comprises an automatic transmission operational range selected at park position to produce said lock condition indicative signal.

13. A height control system as set forth in claim 9, wherein said detector comprises a foot brake switch detective of application of a foot brake to produce said lock condition indicative signal.

14. A height control system as set forth in claim 13, wherein said detector comprises an automatic transmission operational range selected at park position to produce said lock condition indicative signal.

15. A height control system as set forth in claim 7, wherein said controlling means is responsive to said lock condition indicative signal to set a given period of time during which height adjustment is enabled and to disable height adjustment after expiration of said given period of time.

16. A height control system for an automotive suspension system, comprising:

a suspension system disposed between a vehicle body and a suspension member rotatably supporting a drive wheel which is connected to a drive power source via a power train to be rotatingly driven by the output torque of said drive power source, said suspension system including means for varying suspension force to be exerted between said vehicle body and said suspension member, said varying means comprises a hollow chamber communicated with a working fluid source to introduce and discharge working fluid in said hollow chamber for adjusting pressure of working fluid in said hollow chamber, which fluid pressure serves as said suspension force, and a pressure control valve disposed between said working fluid source and said hollow chamber for controlling introduction and discharging of working fluid into and from said hollow chamber for adjusting said suspension force and whereby adjusts said relative distance;

a sensor monitoring a relative distance between said vehicle body and said suspension member for producing a height indicative sensor signal;

a detector for detecting lock condition of said drive wheel and said power train to produce a lock condition indicative signal; and a controlling means for receiving said sensor signal, and checking the value of said sensor signal with respect to a prederermined value for deriving a control signal to operate said varying means to adjust said suspension force for maintaining said relative distance between said vehicle body and said suspension member at a desired value, said controlling means being responsive to said lock condition indicative signal to limit magnitude of height adjustment with a predetermined range.

17. A height control system as set forth in claim 16, wherein said detector monitors brake condition on said road wheel.

18. A height control system as set forth in claim 17, wherein said detector comprises a parking brake switch detective of application of a parking brake to produce said lock condition indicative signal.

19. A height control system as set forth in claim 17, wherein said detector comprises a foot brake switch detective of application of a foot brake to produce said lock condition indicative signal.

20. A height control system as set forth in claim 16, wherein said detector comprises an automatic transmission operational range selected at park position to produce said lock condition indicative signal.

21. A height control system as set forth in claim 17, wherein said detector also comprises an automatic transmission operational range selected at park position to produce said lock condition indicative signal.

22. A height control system as set forth in claim 18, wherein said detector also comprises a foot brake switch detective of application of a foot brake to produce said lock condition indicative signal.

23. A height control system as set forth in claim 22, wherein said detector further comprises an automatic transmission operational range selected at park position to produce said lock condition indicative signal.

24. A height control system as set forth in claim 16, wherein said controlling means is responsive to said lock condition indicative signal to set a given period of time during which height adjustment is enabled and to disable height adjustment after expiration of said given period of time.

25. A height control system for an automotive suspension system, comprising:

a suspension system disposed between a vehicle body and a suspension member rotatably supporting a drive wheel which is connected to a drive power source via a power train to be rotatingly driven by the output torque of said drive power source, said suspension system including means for varying suspension force to be exerted between said vehicle body and said suspension member;

a sensor monitoring a relative distance between said vehicle body and said suspension member for producing a height indicative sensor signal;

a first detector for detecting lock condition of said drive wheel to produce a first lock condition indicative signal;

a second detector for detecting lock condition of said power train to produce a second lock condition indicative signal;

a controlling means for receiving said sensor signal, and checking the value of said sensor signal with respect to a predetermined value for deriving a control signal to operate said varying means to adjust said suspension force for maintaining said relative distance between said vehicle body and said suspension member at a desired value, said controlling means limiting magnitude of height adjustment with a predetermined range when both of said first and second lock condition indicative signals are detected.

26. A height control system as set forth in claim 25, wherein said first detector monitors brake condition on said road wheel.

27. A height control system as set forth in claim 26, wherein said first detector comprises a parking brake switch detective of application of a parking brake to produce said lock condition indicative signal.

28. A height control system as set forth in claim 26, wherein said first detector comprises a foot brake switch detective of application of a foot brake to produce said lock condition indicative signal.

29. A height control system as set forth in claim 25, wherein said second detector comprises an automatic transmission operational range selected at park position to produce said lock condition indicative signal.

30. A height control system as set forth in claim 26, wherein said second detector also comprises an automatic transmission operational range selected at park position to produce said lock condition indicative signal.

31. A height control system as set forth in claim 25, wherein said controlling means is responsive to said lock condition indicative signal to set a given period of time during which height adjustment is enabled and to disable height adjustment after expiration of said given period of time.

* * * * *